US010815317B2

(12) United States Patent
Aida et al.

(10) Patent No.: US 10,815,317 B2
(45) Date of Patent: Oct. 27, 2020

(54) METHOD FOR PRODUCING OLIGOMER AND CATALYST

(71) Applicant: ENEOS Corporation, Tokyo (JP)

(72) Inventors: Fuyuki Aida, Tokyo (JP); Kazuo Tagawa, Tokyo (JP)

(73) Assignee: ENEOS CORPORATION, Tokyo (JP)

(*) Notice: Subject to any disclaimer, the term of this patent is extended or adjusted under 35 U.S.C. 154(b) by 18 days.

(21) Appl. No.: 16/084,797

(22) PCT Filed: Feb. 20, 2017

(86) PCT No.: PCT/JP2017/006183
§ 371 (c)(1),
(2) Date: Sep. 13, 2018

(87) PCT Pub. No.: WO2017/159226
PCT Pub. Date: Sep. 21, 2017

(65) Prior Publication Data
US 2019/0077888 A1 Mar. 14, 2019

(30) Foreign Application Priority Data
Mar. 16, 2016 (JP) ................. 2016-052420

(51) Int. Cl.
C07C 2/32 (2006.01)
C08F 4/70 (2006.01)
C08F 210/16 (2006.01)
C08F 110/02 (2006.01)
B01J 31/22 (2006.01)

(52) U.S. Cl.
CPC .............. *C08F 4/7042* (2013.01); *C07C 2/32* (2013.01); *C08F 4/7006* (2013.01); *C08F 210/16* (2013.01); B01J 31/22 (2013.01); C08F 110/02 (2013.01); C08F 2410/01 (2013.01)

(58) Field of Classification Search
CPC ...... C08F 4/7006; C08F 4/7042; C08F 10/02; B01J 31/22; C07C 2/32
See application file for complete search history.

(56) References Cited

U.S. PATENT DOCUMENTS 6,831,143 B2 * 12/2004 Britovsek ............ C07D 213/53
526/352

FOREIGN PATENT DOCUMENTS

| CN | 101531725 | | 9/2009 |
| CN | 101812145 | A | 8/2010 |
| CN | 102432415 | A | 5/2012 |
| JP | 2000-516295 | A | 12/2000 |
| JP | 2002-302510 | A | 10/2002 |
| JP | 2007-529616 | A | 10/2007 |
| WO | 98/27124 | A1 | 6/1998 |
| WO | 2005/090425 | A1 | 9/2005 |
| WO | 2016/136892 | A1 | 9/2016 |

OTHER PUBLICATIONS

Walter Kaminsky, "New polymers by metallocene catalysis", Institute for Technical and Macromolecular Chemistry, University of Hamburg, Macromol. Chem. Phys., vol. 197, 1996, pp. 3907-3945.
Lynda K. Johnson et al., "New Pd(II)- and Ni(II)-Based Catalysts for Polymerization of Ethylene and a-Olefins", Journal of the American Chemical Society, vol. 117, 1995, pp. 6414-6415.
Brooke L. Small et al., "Iron-Based Catalysts with Exceptionally High Activities and Selectivities for Oligomerization of Ethylene to Linear a-Olefins", Journal of the American Chemical Society, vol. 120, 1998, pp. 7143-7144.
Roland Schmidt et al., "Heterogenized iron(II) complexes as highly active ethene polymerization catalysts", Journal of Molecular Catalysis A: Chemical, vol. 179, 2002, pp. 155-173.
Christian Görl et al., "Bis(arylimino)pyridine iron(III) complexes as catalyst precursors for the oligomerization and polymerization of ethylene", Applied Catalysis A: General, vol. 403, 2011, pp. 25-35.
Konstantin P. Bryliakov et al., "Formation and Nature of the Active Sites in Bis(imino)pyridine Iron-Based Polymerization Catalysts", Organometallics, vol. 28, 2009, pp. 3225-3232.
Daniel J. Arriola et al., "Catalytic Production of Olefin Block Copolymers via Chain Shuttling Polymerization", Science, vol. 312, 2006, pp. 714-719.
Lihua Guo et al., "Substituent Effects of the Backbone in a-Diimine Palladium Catalysts on Homo- and Copolymerization of Ethylene with Methyl Acrylate", Organometallics, vol. 31, Aug. 14, 2012, pp. 6054-6062.
International Search Report issued with respect to Application No. PCT/JP2017/006183, dated Mar. 14, 2017.
International Preliminary Report on Patentability issued with respect to Application No. PCT/JP2017/006183, dated Sep. 27, 2018.
Notice of Allowance in counterpart JP Patent Application No. P2016-052420 dated Jul. 2, 2019.
Thomas Schleis et al., "Ni (II) and Pd( II) complexes of camphor-derived diazadiene ligands: steric bulk tuning and ethylene polymerization", Inorganic Chemistry Communications, Elsevier, vol. 1,1998, p. 431-p. 434.

(Continued)

Primary Examiner — Caixia Lu
(74) Attorney, Agent, or Firm — Greenblum & Bernstein, P.L.C.

(57) ABSTRACT

The present invention provides a method for preparing an oligomer and a catalyst comprising a step of oligomerizing a polymerizable monomer containing an olefin in the presence of a catalyst, which comprises (A) a complex of a diimine compound and at least one metal selected from the group consisting of Group 8 elements, Group 9 elements and Group 10 elements, (B) a mixture of a pyridine diimine compound and an iron salt and/or an iron complex, (C) methylaluminoxane and/or a boron compound, and (D) an organoaluminum compound other than methylaluminoxane and/or an organozinc compound. The components (A), (B), (C) and (D) described above are respectively as defined in the present Description.

4 Claims, No Drawings

(56) References Cited

OTHER PUBLICATIONS

Ting Li et al., "Unsymmetrical α-Diimine Nickel (II) Complex with Rigid Bicyclic Ring Ligand: Synthesis, Characterization, and Ethylene Polymerization in the Presence of AlEt2Cl", Journal of Applied Polymer Science, vol. 108, Dec. 27, 2007, p. 206-p. 210.
Feng-Shou Liu et al., "Thermostable α-Diimine Nickel(II) Catalyst for Ethylene Polymerization: Effects of the Substituted Backbone Structure on Catalytic Properties and Branching Structure of Polyethylene", Macromolecules, vol. 42, Apr. 9, 2009, p. 7789-p. 7796.
Claudio Bianchini et al., "Oligomerisation of Ethylene to Linear α-Olefins by new Cs- and C1-Symmetric [2,6-Bis(imino)pyridyl]iron and cobalt Dichloride Complexes", European Journal of Inorganic Chemistry, Apr. 7, 2003, p. 1620-p. 1631.
Jingdai Wang et al., "Fe(acac)n and Co(acac)n Bearing Different Bis(imino)pyridine Ligands for Ethylene Polymerization and Oligomerization", Journal of Applied Polymer Science, vol. 113, Apr. 27, 2009, p. 2378-p. 2391.

* cited by examiner

METHOD FOR PRODUCING OLIGOMER AND CATALYST

TECHNICAL FIELD

The present invention relates to a method for preparing an oligomer and a catalyst, particularly to a method for preparing an oligomer from a polymerizable monomer containing an olefin and a catalyst.

BACKGROUND ART

As Catalysts used for the copolymerization of ethylene and an α-olefin, catalysts consisting of a metallocene compound and methylaluminoxane, palladium catalysts, iron catalysts and cobalt complexes are known (Non Patent Literatures 1 to 3, Patent Literatures 1 to 3).

Further, iron complexes are also known as the catalyst for ethylene polymerization (Non Patent Literatures 4 to 6).

Further, as catalysts for preparing block copolymers, diethylzinc, a metallocene compound, and a catalyst consisting of a palladium catalyst and dialkylzinc are known (Non Patent Literature 7, Patent Literature 4).

CITATION LIST

Patent Literature

Patent Literature 1: JP 2000-516295 A
Patent Literature 2: JP 2002-302510 A
Patent Literature 3: CN 102432415 A
Patent Literature 4: JP 2007-529616 A

Non Patent Literature

Non Patent Literature 1: "Macromol. Chem. Phys.", Vol. 197, 1996, p. 3907
Non Patent Literature 2: "J. Am. Chem. Soc.", Vol. 117, 1995, p. 6414
Non Patent Literature 3: "J. Am. Chem. Soc.", Vol. 120, 1998, p. 7143
Non Patent Literature 4: "J. Mol. Cat. A: Chemical", Vol. 179, 2002, p. 155
Non Patent Literature 5: "Appl. Cat. A: General", Vol. 403, 2011, p. 25
Non Patent Literature 6: "Organometallics", Vol. 28, 2009, p. 3225
Non Patent Literature 7: "Science", Vol. 312, 2006, p. 714

SUMMARY OF INVENTION

Technical Problem

The present invention's purpose is a method for preparing an oligomer and a catalyst capable of, in the oligomerization of a polymerizable monomer containing an olefin, sufficiently controlling the progress of excessive polymerization.

Solution to Problem

More specifically, the present invention provides a method for preparing an oligomer, comprising a step of oligomerizing a polymerizable monomer containing an olefin in the presence of a catalyst comprising (A) a complex of a diimine compound represented by the following formula (1) and at least one metal selected from the group consisting of Group 8 elements, Group 9 elements and Group 10 elements, (B) a mixture of a pyridine diimine compound represented by the following formula (3) and an iron salt and/or an iron complex represented by the following formula (5), (C) methylaluminoxane and/or a boron compound, and (D) an organoaluminum compound other than methylaluminoxane and/or an organozinc compound.

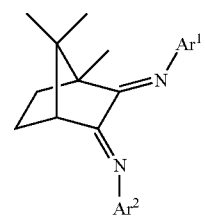

(1)

wherein $Ar^1$ and $Ar^2$ may be the same or different and are respectively a group represented by the following formula (2).

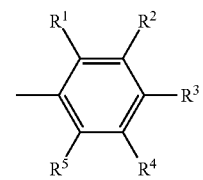

(2)

wherein $R^1$ and $R^5$ may be the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ may be the same or different and are respectively a hydrogen atom or an electron-donating group.

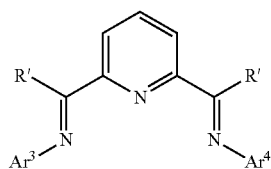

(3)

wherein R' is a hydrocarbyl group having 1 to 6 carbon atoms or an aromatic group having 6 to 12 carbon atoms, a plurality of R' in the same molecule may be the same or different, $Ar^3$ and $Ar^4$ may be the same or different and are respectively a group represented by the following formula (4):

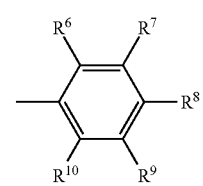

(4)

wherein $R^6$ and $R^{10}$ may be the same or different and are respectively a hydrocarbyl group having 3 to 12 carbon atoms or an aromatic group having 6 to 12 carbon atoms, the total number of carbon atoms of $R^6$ and $R^{10}$ is 6 or more, and $R^7$, $R^8$ and $R^9$ may be the same or different and are respectively a hydrogen atom or an electron-donating group.

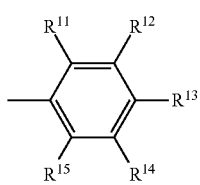
(5)

wherein R is a hydrocarbyl group having 1 to 6 carbon atoms or an aromatic group having 6 to 12 carbon atoms, a plurality of R in the same molecule may be the same or different, $Ar^5$ and $Ar^6$ may be the same or different and are respectively a group represented by the following formula (6), and Y is a chlorine atom or a bromine atom.

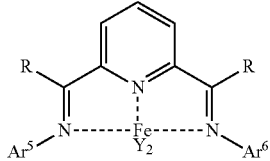
(6)

wherein $R^{11}$ and $R^{15}$ may be the same or different and are respectively a hydrocarbyl group having 3 to 12 carbon atoms or an aromatic group having 6 to 12 carbon atoms, the total number of carbon atoms of $R^{11}$ and $R^{15}$ is 6 or more, and $R^{12}$, $R^{13}$ and $R^{14}$ may be the same or different and are respectively a hydrogen atom or an electron-donating group.

According to the above production method, the progress of excessive polymerization can be sufficiently controlled in the oligomerization of a polymerizable monomer containing an olefin.

In the above preparation method, the number average molecular weight (Mn) of the obtained oligomer can be controlled the range of 200 to 5000.

The organoaluminum compound may be at least one selected from the group consisting of trimethylaluminum, triethylaluminum, triisopropylaluminum, tripropylaluminum, tributylaluminum, triisobutylaluminum, trihexylaluminum, triphenylaluminum, diethylaluminum chloride, ethylaluminum dichloride and ethylaluminum sesquichloride.

The organozinc compound may be at least one selected from the group consisting of dimethylzinc, diethylzinc and diphenylzinc.

Further, the present invention provides a catalyst comprising (A) a complex of a diimine compound represented by the following formula (1) and at least one metal selected from the group consisting of Group 8 elements, Group 9 elements and Group 10 elements, (B) a mixture of a pyridine diimine compound represented by the following formula (3) and an iron salt and/or an iron complex represented by the following formula (5), (C) methylaluminoxane and/or a boron compound, and (D) an organoaluminum compound other than methylaluminoxane and/or an organozinc compound.

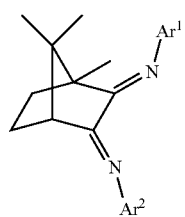
(1)

wherein $Ar^1$ and $Ar^2$ may be the same or different and are respectively a group represented by the following formula (2).

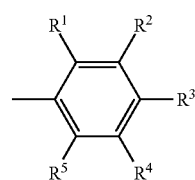
(2)

wherein $R^1$ and $R^5$ may be the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ may be the same or different and are respectively a hydrogen atom or an electron-donating group.

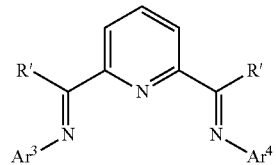
(3)

wherein R' is a hydrocarbyl group having 1 to 6 carbon atoms or an aromatic group having 6 to 12 carbon atoms, a plurality of R' in the same molecule may be the same or different, $Ar^3$ and $Ar^4$ may be the same or different and are respectively a group represented by the following formula (4):

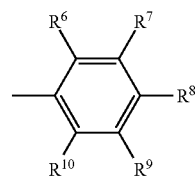
(4)

wherein $R^6$ and $R^{10}$ may be the same or different and are respectively a hydrocarbyl group having 3 to 12 carbon atoms or an aromatic group having 6 to 12 carbon atoms, the total number of carbon atoms of $R^6$ and $R^{10}$ is 6 or more, and $R^7$, $R^8$ and $R^9$ may be the same or different and are respectively a hydrogen atom or an electron-donating group.

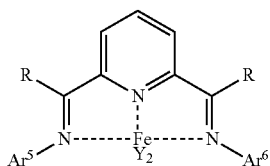

(5)

wherein R is a hydrocarbyl group having 1 to 6 carbon atoms or an aromatic group having 6 to 12 carbon atoms, a plurality of R in the same molecule may be the same or different, $Ar^5$ and $Ar^6$ may be the same or different and are respectively a group represented by the following formula (6), and Y is a chlorine atom or a bromine atom.

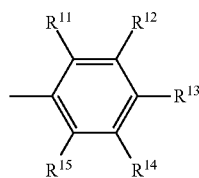

(6)

wherein $R^{11}$ and $R^{15}$ may be the same or different and are respectively a hydrocarbyl group having 3 to 12 carbon atoms or an aromatic group having 6 to 12 carbon atoms, the total number of carbon atoms of $R^{11}$ and $R^{15}$ is 6 or more, and $R^{12}$, $R^{13}$ and $R^{14}$ may be the same or different and are respectively a hydrogen atom or an electron-donating group.

Advantageous Effects of Invention

According to the present invention, the method for preparing an oligomer and a catalyst capable of, in the oligomerization of a polymerizable monomer containing an olefin, sufficiently controlling the progress of excessive polymerization can be provided.

DESCRIPTION OF EMBODIMENTS

Hereinafter, preferred embodiments of the present invention are described in detail.

[Catalyst]

The catalyst for the oligomerization of a polymerizable monomer containing an olefin according to the present embodiment contains the component (A) to the component (D) described below.

<Component (A)>

In the present embodiment, the component (A) is a complex of the diimine compound (ligand) represented by the following formula (1) and at least one metal selected from the group consisting of Group 8 elements, Group 9 elements and Group 10 elements.

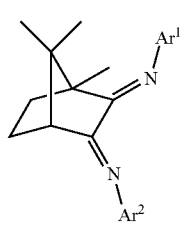

(1)

In the formula (1), $Ar^1$ and $Ar^2$ may be the same or different and are respectively a group represented by the following formula (2).

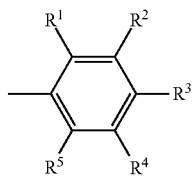

(2)

In the formula (2), $R^1$ and $R^5$ may be the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ may be the same or different and are respectively a hydrogen atom or an electron-donating group.

Note that $Ar^1$ and $Ar^2$ in the same molecule may be the same or different but are preferably the same in light of simplifying the synthesis of the ligand.

Examples of the hydrocarbyl group, having 1 to 5 carbon atoms and represented by $R^1$ and $R^5$, include an alkyl group having 1 to 5 carbon atoms and an alkenyl group having 2 to 5 carbon atoms. The hydrocarbyl group may be linear, branched or cyclic. Further, the hydrocarbyl group may be a monovalent group of a linear or branched hydrocarbyl group bonded to a cyclic hydrocarbyl group.

Examples of the alkyl group containing 1 to 5 carbon atoms include a linear alkyl group having 1 to 5 carbon atoms such as a methyl group, an ethyl group, an n-propyl group, an n-butyl group and an n-pentyl group; a branched alkyl group having 1 to 5 carbon atoms such as an iso-propyl group, an iso-butyl group, a sec-butyl group, a tert-butyl group and a branched pentyl group (including all structural isomers); and a cyclic alkyl group having 1 to 5 carbon atoms such as a cyclopropyl group and a cyclobutyl group.

Examples of the alkenyl group containing 2 to 5 carbon atoms include a linear alkenyl group having 2 to 5 carbon atoms such as an ethenyl group (vinyl group), an n-propenyl group, an n-butenyl group and an n-pentenyl group; a branched alkenyl group having 2 to 5 carbon atoms such as an iso-propenyl group, an iso-butenyl group, a sec-butenyl group, a tert-butenyl group and a branched pentenyl group (including all structural isomers); and a cyclic alkenyl group having 2 to 5 carbon atoms such as a cyclopropenyl group, a cyclobutenyl group and a cyclopentenyl group.

In the light of controlling the molecular weight of the olefin oligomer obtained by the olefin polymerization catalytic reaction, the total number of carbon atoms of $R^1$ and $R^5$ is 1 or more and 5 or less, preferably 1 or more and 4 or less, more preferably 1 or more and 3 or less, further preferably 1 or more and 2 or less, most preferably 1. When the total number of carbon atoms of $R^1$ and $R^5$ is within the above ranges, the production of a polymer having a large molecular weight by the olefin polymerization reaction can be controlled. Particularly, when the total number of carbon atoms of $R^1$ and $R^5$ is 5 or less, the influence of steric hindrance by a substituent on the benzene ring is reduced and the molecular conformation change easily takes place. As a result, the elimination reaction is promoted and the production of a polymer having a large molecular weight is restrained.

Further, in the light of suppressing the influence of steric hindrance by a substituent on the benzene ring, it is preferable that either one of $R^1$ or $R^5$ be a hydrogen atom and the other be a hydrocarbyl group having 1 to 5 carbon atoms.

In the formula (2), $R^2$, $R^3$ and $R^4$ are each independently a hydrogen atom or an electron-donating group. The electron-donating group is not particularly limited and examples include an alkyl group having 1 to 8 carbon atoms, an alkoxy group having 1 to 8 carbon atoms, an aryl group, an aryloxy group, a hydroxy group and a monovalent group of two or more of these groups combined. The alkyl group and the alkoxy group may be either of linear, branched or cyclic. Further, the aryl group and the aryloxy group may have a substituent such as an alkyl group.

Examples of $R^2$, $R^3$ and $R^4$ include specifically a methyl group, an ethyl group, a linear or branched propyl group, a linear or branched butyl group, a linear or branched pentyl group, a linear or branched hexyl group, a cyclohexyl group, a methylcyclohexyl group, a phenyl group, a tolyl group, a xylyl group, a hydroxy group, a methoxy group, an ethoxy group, a linear or branched propoxy group, a linear or branched butoxy group, a linear or branched pentyloxy group, a cyclopentyloxy group, a linear or branched hexyloxy group, a cyclohexyloxy group, a phenoxy group, a tolyloxy group and a xylyloxy group. Among these, a hydrogen atom, a methyl group and a methoxy group are preferable.

Examples of the preferable aspect of the diimine compound represented by the formula (1) include each of the diimine compounds represented by the following formulae (1-1) to (1-3). The diimine compound represented by the formula (1) can be used singly or in combination of two or more.

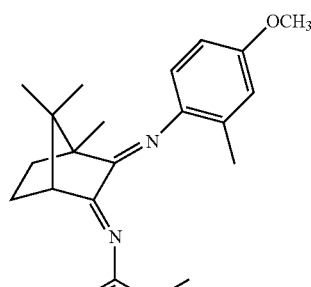

(1-1)

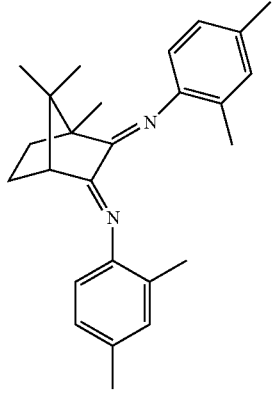

(1-2)

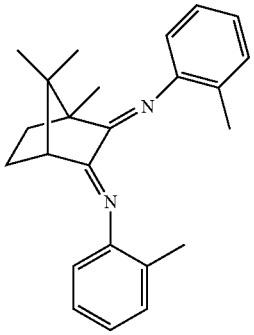

(1-3)

The diimine compound represented by the formula (1) can be synthesized by, for example, dehydrocondensing camphorquinone and an aniline compound having the aromatic group represented by the formula (2). Any synthetic method is employed and an acid catalyst may be used as needed. Examples of the acid catalyst include protonic acids and Lewis acids. Among them, acetic acid, benzene sulfonic acid, paratoluenesulfonic acid, boron trifluoride or salts thereof and organoaluminum compounds are preferable among them.

Examples of the above aniline compound include 2-methylaniline, 2,4-dimethylaniline, 2,6-dimethylaniline, 2,4,6-trimethylaniline, 2-methyl-4-methoxyaniline, 2-ethylaniline, 2,4-diethylaniline, 2,6-diethylaniline, 2,4,6-triethylaniline, 2-ethyl-4-methoxyaniline, 2-propylaniline, 2-isopropylaniline, 2-butylaniline, 2-isobutylaniline and 2-certbutylaniline. These can be used singly or in combination of two or more.

A preferable aspect of the production method of the diimine compound represented by the formula (1) comprises: a first step of dissolving camphorquinone, an aniline compound and an acid catalyst in a solvent and dehydrocondensing by heating under reflux with the solvent, and a second step of carrying out separation and purification treatments of the reaction mixture after the first step to obtain the diimine compound represented by the formula (1).

Examples of the solvent used in the first step include hydrocarbon solvents and alcohol solvents. Examples of the hydrocarbon solvent include hexane, heptane, octane, benzene, toluene, xylene, cyclohexane and methylcyclohexane. Examples of the alcohol solvent include methanol, ethanol and isopropyl alcohol.

The reaction conditions for the first step can be suitably selected in accordance with the kind and amount of the raw material compounds, acid catalyst and solvent.

The separation and purification treatments in the second step is not particularly limited and examples include silica gel column chromatography and recrystallizing method. Particularly, when the organoaluminum compound described above is used as the acid catalyst, it is preferable to mix the reaction solution with a basic aqueous solution to decompose and remove the aluminum and subsequently purify.

The component (A) according to the present embodiment is a complex containing, as the central metal, at least one metal selected from the group consisting of Group 8 elements, Group 9 elements and Group 10 elements. The "Group 8 elements", "Group 9 elements" and "Group 10 elements" used herein are the names based on the IUPAC long periodic table (new periodic table). These elements may sometimes be collectively named as "Group VIII element" based on the short periodic table (old periodic table). More specifically, Group 8 elements, Group 9 elements and Group 10 elements (Group VIII element) are at least one selected from the group consisting of iron, cobalt, nickel, ruthenium, rhodium, palladium and platinum.

Of these, nickel is preferable in the light of a high polymerization activity and availability.

In the preparation method of the complex according to the present embodiment, the mixing method of the diimine compound represented by the formula (1) and at least one metal selected from the group consisting of Group 8 elements, Group 9 elements and Group 10 elements is not particularly limited and examples include (i) a method of adding at least one metal salt (hereinafter, sometimes simply referred to as "salt") selected from the group consisting of Group 8 elements, Group 9 elements and Group 10 elements to a solution with the diimine compound dissolved therein and mixing, (ii) a method of mixing a solution with the diimine compound dissolved therein and a solution with the salt dissolved therein and (iii) a method of physically mixing the diimine compound and the salt without using a solvent.

The method for taking out the complex from the mixture of the diimine compound represented by the formula (1) and at least one metal selected from the group consisting of Group 8 elements, Group 9 elements and Group 10 elements is not particularly limited and examples include (a) a method of distilling off a solvent when the solvent is used in the mixture, and separating the solid matter by filtration, (b) a method of separating the precipitate produced from the mixture by filtration, (c) a method of purifying the precipitate by adding a poor solvent to the mixture and separating by filtration and (d) a method of directly taking out the solvent-free mixture. Subsequently, washing treatment using a solvent capable of dissolving the diimine compound represented by formula (1), washing treatment using a solvent capable of dissolving the metal or recrystallization treatment using a suitable solvent may further be carried out.

Among the above methods, the method of dissolving the diimine compound and the salt using a solvent and mixing (in other words, the methods (i) and (ii)) is industrially preferable, because the method can form the complex in the system and the complex can be directly used, eliminating the necessity of the operation for purifying the produced complex. In other words, the (reaction) mixtures of (i) and (ii) can also be used directly. Alternatively, it is also feasible to separately add to a reactor a solution (or a slurry) of the diimine compound represented by the formula (1) and a solution (or a slurry) of at least one metal selected from the group consisting of Group 8 elements, Group 9 elements and Group 10 elements.

Examples of the salt of at least one metal selected from the group consisting of Group 8 elements, Group 9 elements and Group 10 elements include iron(II) chloride, iron(III) chloride, iron(II) bromide, iron(III) bromide, iron(II) acetylacetonate, iron(III) acetylacetonate, iron(II) acetate, iron (III) acetate, cobalt(II) chloride, cobalt(III) chloride, cobalt (II) bromide, cobalt(III) bromide, cobalt(II) acetylacetonate, cobalt(III) acetylacetonate, cobalt(II) acetate, cobalt(III) acetate, nickel(II) 2-ethylhexanoate, nickel(II) chloride, nickel(II) bromide, nickel(II) acetylacetonate, palladium chloride, palladium acetylacetonate and palladium acetate. These salts having a solvent or water may be used. For example, complexes having an organic molecule coordinated such as a nickel chloride dimethoxyethane complex, (nickel(II) chloride-dimethoxyethane complex) can also be preferably used.

The solvent for allowing the compound represented by the formula (1) to contact the metal is not particularly limited. Both nonpolar solvents and polar solvents can be used. Examples of the nonpolar solvent include hydrocarbon solvents such as hexane, heptane, octane, benzene, toluene, xylene, cyclohexane and methylcyclohexane. Examples of the polar solvent include polar protic solvents such as alcohol solvents and polar aprotic solvents such as tetrahydrofuran. Examples of the alcohol solvent include methanol, ethanol and isopropyl alcohol. Particularly when the mixture is used as the olefin polymerization catalyst, it is preferable to use a hydrocarbon solvent that substantially does not affect the olefin polymerization.

In the complex according to the present embodiment, the content ratio of the diimine compound represented by the formula (1) and at least one metal selected from the group consisting of Group 8 elements, Group 9 elements and Group 10 elements is not particularly limited and the unreacted diimine compound and/or metal may be contained. The ratio of the diimine compound/metal is, in a molar ratio, preferably 0.2/1 to 5/1, more preferably 0.3/1 to 3/1, further preferably 0.5/1 to 2/1. When a ratio of the diimine compound/metal is 0.2/1 or more, the olefin polymerization reaction by the metal to which a ligand is not coordinated can be controlled, thus enabling an intended olefin polymerization reaction to progress selectively. When a ratio of the diimine compound/metal is 5/1 or less, the coordination and the like by excessive ligands is controlled, thus further increasing the activity of the olefin polymerization reaction.

<Component (B)>

In the present embodiment, the component (B) is a mixture of a pyridine diimine compound represented by the following formula (3) and an iron salt and/or an iron complex represented by the following formula (5).

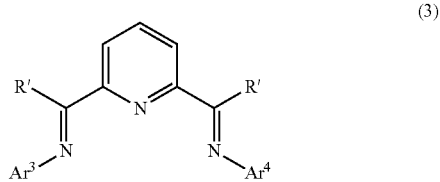

(3)

In the formula (3), R' is a hydrocarbyl group having 1 to 6 carbon atoms or an aromatic group having 6 to 12 carbon atoms, a plurality of R' in the same molecule may be the same or different, $Ar^3$ and $Ar^4$ may be the same or different and are respectively a group represented by the following formula (4).

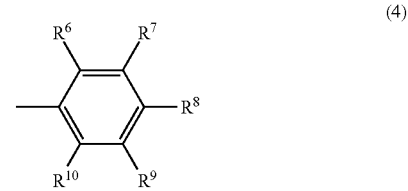

(4)

In the formula (4), $R^6$ and $R^{10}$ may be the same or different and are respectively a hydrocarbyl group having 3 to 12 carbon atoms or an aromatic group having 6 to 12 carbon atoms, the total number of carbon atoms of $R^6$ and $R^{10}$ is 6 or more, and $R^7$, $R^8$ and $R^9$ may be the same or different and are respectively a hydrogen atom or an electron-donating group.

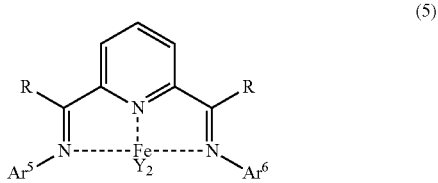

(5)

In the formula (5), R is a hydrocarbyl group having 1 to 6 carbon atoms or an aromatic group having 6 to 12 carbon atoms, a plurality of R in the same molecule may be the same or different, $Ar^5$ and $Ar^6$ may be the same or different and are respectively a group represented by the following formula (6), and Y is a chlorine atom or a bromine atom.

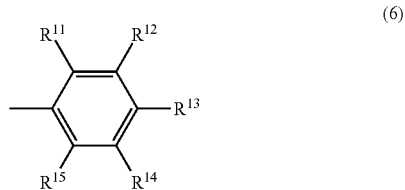

(6)

In the formula (6), $R^{11}$ and $R^{15}$ may be the same or different and are respectively a hydrocarbyl group having 3 to 12 carbon atoms or an aromatic group having 6 to 12 carbon atoms, the total number of carbon atoms of $R^{11}$ and $R^{15}$ is 6 or more, and $R^{12}$, $R^{13}$ and $R^{14}$ may be the same or different and are respectively a hydrogen atom or an electron-donating group.

In the formula (3), R' is a hydrocarbyl group having 1 to 6 carbon atoms or an aromatic group having 6 to 12 carbon atoms, a plurality of R' in the same molecule may be the same or different. Examples of the hydrocarbyl group having 1 to 6 carbon atoms include an alkyl group having 1 to 6 carbon atoms and an alkenyl group having 2 to 6 carbon atoms. The hydrocarbyl group may be linear, branched or cyclic. Further, the hydrocarbyl group may be a monovalent group of a linear or branched hydrocarbyl group bonded to a cyclic hydrocarbyl group.

Examples of the alkyl group having 1 to 6 carbon atoms include a linear alkyl group having 1 to 6 carbon atoms such as a methyl group, an ethyl group, an n-propyl group, an n-butyl group, an n-pentyl group and an n-hexyl group; a branched alkyl group having 1 to 6 carbon atoms such as an iso-propyl group, an iso-butyl group, a sec-butyl group, a tert-butyl group, a branched pentyl group (including all structural isomers) and a branched hexyl group (including all structural isomers); and a cyclic alkyl group having 1 to 6 carbon atoms such as a cyclopropyl group, a cyclobutyl group and a cyclohexyl group.

Examples of the alkenyl group having 2 to 6 carbon atoms include a linear alkenyl group having 2 to 6 carbon atoms such as an ethenyl group (vinyl group), an n-propenyl group, an n-butenyl group, an n-pentenyl group and an n-hexenyl group; a branched alkenyl group having 2 to 6 carbon atoms such as an iso-propenyl group, an iso-butenyl group, a sec-butenyl group, a tert-butenyl group, a branched pentenyl group (including all structural isomers) and a branched hexenyl group (including all structural isomers); and a cyclic alkenyl group having 2 to 6 carbon atoms such as a cyclopropenyl group, a cyclobutenyl group, a cyclopentenyl group and a cyclohexenyl group.

Examples of the aromatic group having 6 to 12 carbon atoms include a phenyl group, a tolyl group, a xylyl group and a biphenyl group.

In the formula (3), $Ar^3$ and $Ar^4$ may be the same or different and are respectively a group represented by the formula (4). Note that $Ar^3$ and $Ar^4$ in the same molecule may be the same or different but are preferably the same in the light of simplifying the synthesis of the pyridine diimine compound.

In the formula (4), $R^6$ and $R^{10}$ may be the same or different and are respectively a hydrocarbyl group having 3 to 12 carbon atoms or an aromatic group having 6 to 12 carbon atoms, and the total number of carbon atoms of $R^6$ and $R^1$ is 6 or more.

Examples of the hydrocarbyl group having 3 to 12 carbon atoms include an alkyl group having 3 to 12 carbon atoms and an alkenyl group having 3 to 12 carbon atoms. Examples of the alkyl group having 3 to 12 carbon atoms include a linear alkyl group having 3 to 12 carbon atoms such as an n-propyl group, an n-butyl group, an n-pentyl group, an n-hexyl group, an n-octyl group, an n-decyl group and an n-dodecyl group; a branched alkyl group having 3 to 12 carbon atoms such as an iso-propyl group, an iso-butyl group, a sec-butyl group, a tert-butyl group and a branched pentyl group (including all structural isomers); and a cyclic alkyl group having 3 to 12 carbon atoms such as a cyclopropyl group, a cyclobutyl group and a cyclohexyl group. Examples of the alkenyl group having 3 to 12 carbon atoms include a linear alkenyl group having 3 to 12 carbon atoms such as an n-propenyl group, an n-butenyl group, an n-pentenyl group, an n-hexenyl group, an n-octenyl, an n-decenyl and an n-dodecenyl group; a branched alkenyl group having 3 to 12 carbon atoms such as an iso-propenyl group, an iso-butenyl group, a sec-butenyl group, a tert-butenyl group and a branched pentenyl group (including all structural isomers); and a cyclic alkenyl group having 3 to 12 carbon atoms such as a cyclopropenyl group, a cyclobutenyl group and a cyclopentenyl group.

Examples of the aromatic group having 6 to 12 carbon atoms include a phenyl group, a tolyl group, a xylyl group and a biphenyl group.

In the formula (4), $R^7$, $R^8$ and $R^9$ may be the same or different and are respectively a hydrogen atom or an electron-donating group. The electron-donating group is not particularly limited and examples include an alkyl group having 1 to 8 carbon atoms, an alkoxy group having 1 to 8 carbon atoms, an aryl group, an aryloxy group, a hydroxy group and a monovalent group of two or more of these groups combined. The alkyl group and the alkoxy group may be either of linear, branched or cyclic. Further, the aryl group and the aryloxy group may have a substituent such as an alkyl group.

Examples of $R^7$, $R^8$ and $R^9$ include specifically a methyl group, an ethyl group, a linear or branched propyl group, a linear or branched butyl group, a linear or branched pentyl group, a linear or branched hexyl group, a cyclohexyl group, a methylcyclohexyl group, a phenyl group, a tolyl group, a xylyl group, a hydroxy group, a methoxy group, an ethoxy group, a linear or branched propoxy group, a linear or branched butoxy group, a linear or branched pentyloxy group, a cyclopentyloxy group, a linear or branched hexyloxy group, a cyclohexyloxy group, a phenoxy group, a tolyloxy group and a xylyloxy group. Among these, a hydrogen atom, a methyl group and a methoxy group are preferable.

Examples of the iron salt include iron(II) chloride, iron (III) chloride, iron(II) bromide and iron(III) bromide. Further, these salts having crystallization water or other ligands coordinated may also be used.

In the formula (5), R is a hydrocarbyl group having 1 to 6 carbon atoms or an aromatic group having 6 to 12 carbon atoms, and a plurality of R in the same molecule may be the same or different.

Specific examples of R include the same as those described in R' of the above formula (3).

In the formula (5), $Ar^5$ and $Ar^6$ may be the same or different and are respectively a group represented by the formula (6). Note that $Ar^5$ and $Ar^6$ in the same molecule may be the same or different but are preferably the same in the light of simplifying the synthesis of the ligand.

In the formula (6), and $R^{15}$ may be the same or different and are respectively a hydrocarbyl group having 3 to 12 carbon atoms or an aromatic group having 6 to 12 carbon atoms, the total number of carbon atoms of $R^{11}$ and $R^{15}$ is 6 or more. Specific examples of $R^{11}$ and $R^{15}$ include the same as those described respectively in $R^6$ and $R^{10}$ in the above formula (4).

In the formula (6), $R^{12}$, $R^{13}$ and $R^{14}$ may be the same or different and are respectively a hydrogen atom or an electron-donating group. Specific examples of $R^{12}$, $R^{13}$ and $R^{14}$ include the same as those described respectively in $R^7$, $R^8$ and $R^9$ in the above formula (4).

Examples of the preferable aspect of the iron complex represented by the formula (5) include each of the iron complexes represented by the following formulae (5-1) to (5-4). The iron complex represented by the formula (5) can be used singly or in combination of two or more.

(5-1)

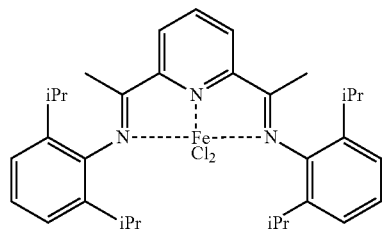

(5-2)

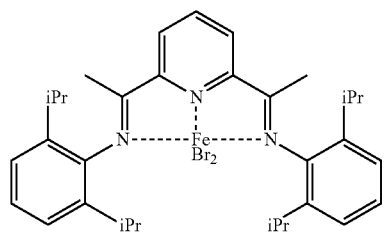

(5-3)

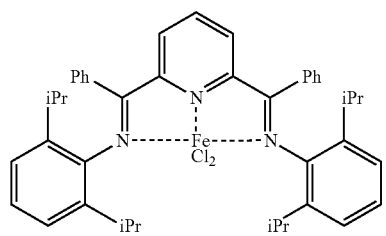

(5-4)

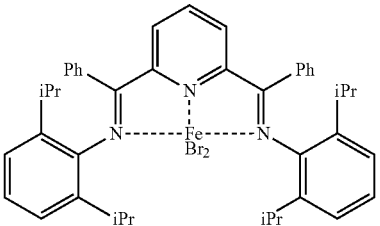

The iron complex represented by the formula (5) can be obtained, for example, from the pyridine diimine compound represented by the formula (3) and an iron salt.

In the preparation method of the iron complex represented by the formula (5), the mixing method of the pyridine diimine compound represented by the formula (3) and the iron salt is not particularly limited. Examples include:

(i) a method of adding the iron salt to a solution with the pyridine diimine compound dissolved therein and mixing, (ii) a method of mixing a solution with the pyridine diimine compound dissolved therein and a solution with the iron salt dissolved therein, and (iii) a method of physically mixing the pyridine diimine compound and the iron salt without using a solvent.

Further, the method for taking out the iron complex represented by the formula (5) from the mixture of the pyridine diimine compound represented by the formula (3) and the iron salt is not particularly limited. Examples include (a) a method of distilling off a solvent when the solvent is used in the mixture, and separating the solid matter by filtration, (b) a method of separating the precipitate produced from the mixture by filtration, (c) a method of purifying the precipitate by adding a poor solvent to the mixture and separating by filtration, and (d) a method of directly taking out the solvent-free mixture. Subsequently, washing treatment using a solvent capable of dissolving the pyridine diimine compound represented by formula (3), washing treatment using a solvent capable of dissolving the metal, or recrystallization treatment using a suitable solvent may further be carried out.

Among the above methods, the method of dissolving the pyridine diimine compound and the iron salt using a solvent and mixing (in other words, the methods (i) and (ii)) can form the iron complex in the system and be directly used, eliminating the necessity of the operation for purifying the produced iron complex, hence industrially preferable. In other words, the mixtures of (i) and (ii) can also be used directly. Alternatively, it is also feasible to separately add to a reactor a solution (or a slurry) of the pyridine diimine compound represented by the formula (3) and a solution (or a slurry) of the iron salt.

Further, the solvent for allowing the pyridine diimine compound represented by the formula (3) to contact the iron salt is not particularly limited. Both nonpolar solvents and polar solvents can be used.

Examples of the nonpolar solvent include hydrocarbon solvents such as hexane, heptane, octane, benzene, toluene, xylene, cyclohexane and methylcyclohexane. Examples of the polar solvent include polar protic solvents such as alcohol solvents and polar aprotic solvents such as tetrahydrofuran. Examples of the alcohol solvent include methanol, ethanol and isopropyl alcohol. Particularly when the mixture is used as the component (B), it is preferable to use a hydrocarbon solvent that substantially does not affect the olefin polymerization.

In the component (B) according to the present embodiment, the content ratio of the pyridine diimine compound represented by the formula (3) and the iron salt is not particularly limited. The unreacted pyridine diimine compound and/or iron salt may be contained in the component (B). The ratio of the pyridine diimine compound/iron salt is, in a molar ratio, preferably 0.2/1 to 5/1, more preferably 0.3/1 to 3/1, further preferably 0.5/1 to 2/1. When a ratio of the pyridine diimine compound/iron salt is 0.2/1 or more, the olefin polymerization reaction by the iron salt to which a ligand is not coordinated can be controlled, thus enabling an intended olefin polymerization reaction to progress more selectively. When a ratio of the pyridine diimine compound/iron salt is 5/1 or less, the coordination and the like by excessive ligands is controlled, thus further increasing the activity of the olefin polymerization reaction.

If the pyridine diimine compound had two imine moieties being both the E-isomers, the pyridine diimine compound containing the Z-isomer might be contaminated. Of course, it is preferable that both moieties in the pyridine diimine compound are both the E-isomers. The pyridine diimine compound containing the Z-isomer is not likely to form a complex with a metal. Then, after being allowed to form a complex in the system, the Z-isomer can be easily removed at the purification step such as solvent washing.

The pyridine diimine compound represented by the formula (3) can be synthesized by, for example, dehydrocondensing a pyridine dicarbonyl compound and an aniline compound. Any synthetic method is employed. An acid catalyst may be used as needed. Examples of the acid catalyst include protonic acids and Lewis acids, of which acetic acid, benzene sulfonic acid, paratoluenesulfonic acid, boron trifluoride or salts thereof and organoaluminum compounds are preferable.

Examples of the above pyridine dicarbonyl compound include 2,6-diacetylpyridine and 2,6-dibenzoylpyridine.

Examples of the above aniline compound include 2,6-dipropylaniline, 2,6-diisopropylaniline, 2,6-dibutylaniline, 2,6-diisobutylaniline, 2,6-di-tert-butylaniline, 2,6-dipropyl-4-methylaniline, 2,6-diisopropyl-4-methylaniline, 2,6-dibutyl-4-methylaniline, 2,6-diisobutyl-4-methylaniline and 2,6-di-tert-butyl-4-methyaniline. These can be used singly or in combination of two or more. Among these, 2,6-diisopropylaniline is preferable in the light of easy availability of raw materials.

A preferable aspect of the preparation method of the pyridine diimine compound represented by the formula (3) comprises:

a first step of dissolving the pyridine carbonyl compound, an aniline compound and an acid catalyst in a solvent and dehydrocondensing by heating under reflux with the solvent, and a second step of carrying out separation and purification treatments of the reaction mixture after the first step to obtain the pyridine diimine compound represented by the formula (3).

Examples of the solvent used in the first step include hydrocarbon solvents and alcohol solvents. Examples of the hydrocarbon solvent include hexane, heptane, octane, benzene, toluene, xylene, cyclohexane and methylcyclohexane. Examples of the alcohol solvent include methanol, ethanol and isopropyl alcohol.

The reaction conditions for the first step can be suitably selected in accordance with the kind and amount of the raw material compounds, acid catalyst and solvent.

The separation and purification treatments in the second step are not particularly limited and examples include silica gel column chromatography and recrystallizing method. Particularly, when the organoaluminum compound described above is used as the acid catalyst, it is preferable to mix the reaction solution with a basic aqueous solution to decompose and remove the aluminum and subsequently purify.

<Component (C)>

In the present embodiment, the component (C) is methylaluminoxane and/or a boron compound.

For methylaluminoxane, a commercial product diluted with a solvent can be used and those wherein trimethylaluminum is partially hydrolyzed in a solvent can also be used. When unreacted trimethylaluminum remains in the methylaluminoxane, the unreacted trimethylaluminum may be used as the component (D) to be described below in detail, or may be used as dried methylaluminoxane obtained by distilling off the trimethylaluminum and the solvent under reduced pressure. Further, modified methylaluminoxane obtained by allowing trialkylaluminum other than trimethylaluminum such as triisobutylaluminum to coexist at the time of the partial hydrolysis of trimethylaluminum and be co-partially hydrolyzed can also be used. Similarly in this case, when remaining trialkylaluminum is present, the unreacted trialkylaluminum may be used as the component (D) to be described below in detail, or may be used as dried modified methylaluminoxane obtained by distilling off the trialkylaluminum and the solvent.

Examples of the boron compound include an aryl boron compound such as tris pentafluorophenyl borane. Further, for the boron compound, boron compounds having anionic species can be used. Examples include aryl borates such as tetrakis(pentafluorophenyl)borate and tetrakis(3,5-trifiuoromethylphenyl)borate. Specific examples of the aryl borate include lithium tetrakis(pentafluorophenyl)borate, sodium tetrakis(pentafluorophenyl)borate, N,N-dimethylanilinium tetrakis(pentafluorophenyl)borate, trityl tetrakis(pentafluorophenyl)borate, lithium tetrakis(3,5-trifluoromethylphenyl)borate, sodium tetrakis(3,5-trifiuoromethylphenyl)borate, N,N-dimethylanilinium tetrakis(3,5-trifluoromethylphenyl)borate and trityl tetrakis(3,5-trifluoromethylphenyl)borate. Among these, N,N-dimethylanilinium tetrakis(pentafluorophenyl)borate, trityl tetrakis(pentafluorophenyl)borate, N,N-dimethylanilinium tetrakis(3,5-trifluoromethylphenyl)borate or trityl tetrakis(3,5-trifluoromethylphenyl)borate is preferable. These boron compounds can be used singly or in combination of two or more.

<Component (D)>

In the present embodiment, the component (D) is an organoaluminum compound other than methylaluminoxane and/or an organozinc compound.

Specific examples of the organoaluminum compound include trimethylaluminum, triethylaluminum, triisopropylaluminum, tripropylaluminum, tributylaluminum, triisobutylaluminum, trihexylaluminum, triphenylaluminum, diethylaluminum chloride, ethylaluminum dichloride and ethylaluminum sesquichloride. These organoaluminum compounds can be used singly or in combination of two or more.

Specific examples of the organozinc compound include alkylzincs such as dimethylzinc and diethylzinc, and aryl zincs such as diphenylzinc. Alternatively, the organozinc compound may be formed in the reaction system by allowing zinc halide such as zinc chloride, zinc bromide or zinc iodide to act on alkyllithium, allyl Grignard, alkyl Grignard or the organoaluminum compound below. These organozinc compounds can be used singly or in combination of two or more.

It is preferable that the content ratio of the above component (A) to the component (B) in the catalyst be, in a molar ratio, (A):(B)=1:10 to 10:1. When a content ratio of the component (A) to the component (B) is within the above range, the progress of the homopolymerization by each component can be more notably controlled and thereby an oligomer can be produced more efficiently.

Further, when the total number of moles of a content of the component (A) and the component (B) is defined as Y, it is preferable for the content ratio of the Y to the component (C) to be, in a molar ratio, Y:(C–A1)=1:10 to 1:1000, more preferable to be 1:20 to 1:500, in the case of only methylaluminoxane being used as the component (C). When the content ratio of the total amount of the component (A) and the component (B) to (C–A1) is within the above ranges, factors of the increase in costs can be reduced while expressing the more sufficient polymerization activity. Note that (C–A1) represents the number of moles of the aluminum atom in methylaluminoxane.

When meanwhile only the boron compound is used as the component (C), it is preferable that, in a molar ratio, Y:(C–B)=0.1:1 to 10:1, more preferable to be 0.5:1 to 2:1. When the content ratio of the total amount of the component (A) and the component (B) to (C–B) is within the above ranges, factors of the increase in costs can be reduced while expressing the more sufficient polymerization activity. Note that (C–B) represents the number of moles of the boron compound. When only the boron compound is used as the component (C), it is particularly preferable to use an alkyl complex as the component (A) and the component (B) or add an operation to convert to an alkyl complex. Examples of the method for converting to an alkyl complex include, in the case of conversion to a methyl complex, a method wherein the component (A) or the component (B) is allowed to contact an organoaluminum compound such as trimethylaluminum, an organozinc compound such as dimethylzinc, an organolithium compound such as methyllithium or a Grignard compound such as methylmagnesium chloride, thereby being converted to a methyl complex of the component (A) or the component (B). Note that as the organoaluminum compounds and the organozinc compounds listed herein, those described in the above (D) may be used.

When methylaluminoxane and the boron compound are used in combination as the component (C), it is preferable that, in a molar ratio, Y:(C–A1)=1:1 to 1:100 and Y:(C–B)=1:1 to 1:10, more preferable that Y: (C–A1)=1:1 to 1:50 and Y:(C–B)=1:1 to 1:2. When the content ratio of the total amount of the component (A) and the component (B) to (C–A1) and the content ratio of the total amount of the component (A) and the component (B) to (C–B) are within the above ranges, factors of the increase in costs can be reduced while expressing the more sufficient polymerization activity. Further, the conversion to an alkyl complex of the component (A) and the component (B) described above can also be carried out simultaneously.

Further, it is preferable for the content ratio of the above Y to the component (D) to be, in a molar ratio, Y:(D)=1:1 to 1:1000, more preferable to be 1:10 to 1:800. When the content ratio of the total amount of the component (A) and the component (B) to the component (D) is within the above ranges, the effect of chain transfer polymerization by the component (A) and the component (B) is notably demonstrated to thereby more notably reduce the progress of the homopolymerization by the component (A) and the component (B) respectively and thus an oligomer having a suitable molecular weight can be more efficiently produced. Note that the above content ratio of the component (D) represents, when an organoaluminum compound is used as the component (D), the number of moles of the aluminum atom in the organoaluminum compound.

Note that the method for preparing the catalyst containing the component (A) to the component (D) described above is not particularly limited, and the component (A) to the component (D) described above may be allowed to contact at all once or in any order. Examples of the method for allowing each component to contact in any order include a method wherein the component (A) to the component (C) are allowed to contact, followed by allowing the component (D) to contact. Further, for example, those wherein the component (A) to the component (C) have been in contact and the component (D) may be introduced to a reactor separately.

[Method for Producing an Oligomer]

The method for preparing an oligomer in the present embodiment comprises a step of oligomerizing a polymerizable monomer containing an olefin in the presence of the catalyst of the present embodiment described above.

Examples of the olefin include ethylene and α-olefins. Examples of the α-olefin include propylene, 1-butene, 1-pentene, 1-hexene, 1-octene, 1-decene, 1-dodecene, and those having a branch such as a methyl group at a position other than the 2-position of the α-olefin such as 4-methyl-1-pentene.

The oligomer obtained by the preparation method according to the present embodiment may be a homopolymer of one of the above olefins or a copolymer of two or more. The oligomer may be, for example, a homopolymer of ethylene, a homopolymer of propylene or a copolymer of ethylene and propylene. Further, the oligomer may further contain a structural unit derived from a monomer other than the olefins.

In the case of oligomerizing a polymerizable monomer including ethylene and an α-olefin, the feed ratio of ethylene to the α-olefin contacting to the catalyst is not particularly limited. But it is preferable to be, in a molar ratio, ethylene: α-olefin=1000:1 to 1:1000, more preferable to be 100:1 to 1:100. Ethylene and α-olefins have different reactivities, so that the reactivity ratio can be examined using Fineman-Ross method and the like to suitably determine the feed ratio of ethylene to an α-olefin to be fed from the composition ratio of a desired product.

The polymerizable monomer used in the present embodiment may be those consisting of ethylene or α-olefins, may be those consisting of ethylene and α-olefins, or may further contain monomers other than ethylene and α-olefins. Further, one aspect of the production method according to the present embodiment is a method for introducing the polymerizable monomer to a reactor filled with the catalyst. The introduction method of the polymerizable monomer to a reactor is not particularly limited and, when the polymerizable monomer is a monomer mixture containing two or more olefins, the monomer mixture may be introduced to a reactor or each of the polymerizable monomers may be introduced separately.

Further, a solvent may be used at the time of oligomerization. For the solvent, it is preferable to be a nonpolar solvent in the light of carrying out a satisfactory polymerization reaction. Examples of the nonpolar solvent include normal hexane, isohexane, heptane, octane, isooctane, cyclohexane, methylcyclohexane, benzene, toluene and xylene.

The reaction temperature in the present embodiment is not particularly limited but, for example, it is preferable to be from 0 to 100° C., more preferable to be from 10 to 90° C., further preferable to be from 20 to 80° C. When a reaction temperature is 0° C. or more, the reaction can be carried out efficiently without needing a great amount of energy for cooling, whereas when a reaction temperature is 100° C. or less, the lowering of the catalystic activity can be suppressed. Furthermore, the reaction pressure is not particularly limited but it is preferable to be 100 kPa to 5 MPa. The reaction time is not particularly limited but it is preferable, for example, to be 1 minute to 24 hours.

In the present embodiment, the "oligomer" means a polymer having a number average molecular weight (Mn) of, for example, 200 to 5000, preferably 300 to 4500, more preferably 400 to 4000. The dispersity is the ratio of a weight average molecular weight (Mw) to Mn, represented as Mw/Mn, and is preferably 1.0 to 5.0, more preferably 1.1 to 3.0. Note that Mn and Mw of the oligomer can be determined, for example, in terms of polystyrene standard based on a calibration curve using a GPC system.

The preparation method according to the present embodiment is useful as the production method of base materials for a lubricating oil such as olefin oligomer waxes, poly α-olefin (PAO). Further, the oligomer to be obtained by the preparation method according to the present embodiment can be preferably used, for example, as a component for a lubricating oil composition.

EXAMPLES

Hereinafter, the present invention is illustrated with reference to Examples, but the following Examples do not intend to limit the present invention.

[Preparation of Ingredients]

Camphorquinone, a solution of trimethylaluminum in toluene and 2-methyl-4-methoxyaniline, 2,6-diacetylpyridine and 2,6-diisopropylaniline, products of Tokyo Chemical Industry Co., Ltd., were used as received. Nickel(II) acetylacetonate, a product of Aldrich, and methylaluminoxane, a product of Tosoh Finechem Corporation, TMAO-341, were used as received. Diethylzinc, a toluene solution of Nippon Aluminum Alkyls, Ltd. was used as received.

For ethylene, high purity liquefied ethylene, a product of Sumitomo Seika Chemicals, Co., Ltd., was used with being dried through molecular sieve 4 A.

For toluene as the solvent, dry toluene, a product of Wako Pure Chemical Industries, Ltd., was used as received.

[Measurement of the Number Average Molecular Weight (Mn) and the Weight Average Molecular Weight (Mw)]

Two columns (a product of Polymer Laboratories Ltd., tradename: PL gel 10 μm MIXED-B LS) were connected to a high temperature GPC apparatus (a product of Polymer Laboratories Ltd., tradename: PL-220) with refractive index detector. 5 ml of an orthodichlorobenzene solvent was added to 5 mg of a sample and stirred with heating at 140° C. for about 1 hour. The thus dissolved sample was measured at a flow rate set to be 1 ml/min and a column oven temperature to be 140° C. The molecular weight conversion was carried out, calibrated with polystyrene standards.

[Catalytic Efficiency Calculation]

The catalytic efficiency was calculated by dividing the weight of the obtained oligomer by the number of moles of the catalyst fed.

Production Example 1: Synthesis of Diimine Compound (1-1)

2-Methyl-4-methoxyaniline (1.276 g, 9.3 mmol, FM=137) was introduced to a 100 ml flask under a nitrogen atmosphere and dissolved in 20 ml of dry toluene. A solution of trimethylaluminum in toluene (1.8 M, 5.2 ml, 9.3 mmol) was slowly added to the solution and reacted for 2 hours by heating under reflux with toluene. After cooling the reaction solution to room temperature, (1s)-(+)-camphorquinone (0.773 g, 4.7 mmol, FM=166) was added thereto and heated again to reflux for 6 hours.

After completing the reaction, the reaction mixture was cooled to room temperature. A 5%-NaOH aqueous solution was added to the mixture to completely decompose aluminum. The NaOH layer was separated using a separating funnel from the solution thus divided into two layers, then the organic layer was washed with brine. The washed toluene solution was dried over anhydrous magnesium sulfate. After filtrating the inorganic substances, the toluene solution was condensed using an evaporator. The residue was purified by silica gel column chromatography (hexane/ethyl acetate=10/1) to give the intended diimine compound (1-1) in a yield of 72%. Note that the purity was confirmed by GC and the peak at MS 404 was also confirmed by GC-MS. The obtained diimine compound (1-1) was diluted with toluene to be 10 mM and hermetically stored.

Production Example 2: Synthesis of Iron Complex (5-1)

60 ml of dry toluene was introduced to a 100 ml flask under a nitrogen atmosphere, and further 2,6-diisopropylaniline (1.063 g, 6 mmol), 2,6-diacetylpiridine (0.4575 g, 2.8 mmol) and a catalystic amount of paratoluenesulfonic acid were added. The mixture was stirred with heating for 10 hours using a Dean-Stark water separator. The reaction mixture was cooled to room temperature and the toluene was removed using an evaporator. Ethanol (40 ml) was added to the remained solid content and the insoluble solid was separated by filtration. The remained insoluble solid was washed again with ethanol to thereby obtain the pyridine diimine compound as the precursor of the iron complex (5-1) in a yield of 75%. Note that the purity was confirmed by GC and the peak at MS401 was also confirmed by GC-MS.

16 mg of iron(II) chloride tetrahydrate ($FeCl_2 \cdot 4H_2O$) was introduced to a 50 ml Schlenk flask under a nitrogen atmosphere, and 5 ml of tetrahydrofuran was added and the mixture was thoroughly stirred to dissolve. 27 mg of the pyridine diimine compound synthesized above was dissolved in 5 ml of dry tetrahydrofuran in a 10 ml flask. A solution of this pyridine diimine compound was slowly added to the iron chloride solution prepared earlier. The color of yellowish liquid was instantaneously turned to blue to dark navy color. Stirring was continued for 1 hour without further treatment, tetrahydrofuran was distilled off under reduced pressure so as not to be exposed to the air from the Schlenk flask while inside the system was filled with nitrogen. The remained solid was taken out under a nitrogen atmosphere and washed thoroughly with ethanol to dissolve out the remained iron chloride, further washed with diethyl ether and dried without further treatment to thereby obtain the iron complex (5-1) in a yield of 30%. The obtained iron complex (5-1) was diluted with toluene to 10 mM.

Production Example 3: Preparation of a Solution of Nickel 2-ethylhexanoate in Toluene Commercial nickel 2-ethylhexanoate was diluted with dry toluene to 10 mM under a nitrogen atmosphere.

Example 1

20 ml of dry toluene was introduced to a 50 ml flask under a nitrogen gas stream. To the flask, a solution of the diimine compound (1-1) in toluene (1 μmol), a solution of nickel 2-ethylhexanoate in toluene (1 μmol) and further a solution of the iron complex (5-1) in toluene (1 μmol) were added. To the solution, a solution of methylaluminoxane in hexane (Al 3.64 M) in a 100 equivalent amount to the iron complex in terms of aluminum atom was added and the total solution was named as a solution (a).

A 660 ml autoclave equipped with an electromagnetic stirrer was thoroughly dried at 110° C. under reduced pressure in advance. Subsequently, dry toluene (80 ml) was introduced into the autoclave under a nitrogen gas stream, further a solution of diethylzinc in toluene (1 M) in a 500 equivalent amount to the iron complex in terms of zinc atom was added. Then a temperature was adjusted to 30° C. To this solution, the solution (a) prepared earlier was added to thereby obtain a catalyst-containing solution (b). Ethylene at 0.19 MPa was continuously introduced at 30° C. to the autoclave containing the solution (b). The ethylene introduction was halted 30 minutes later, the unreacted ethylene in the autoclave was purged with nitrogen. A very small amount of ethanol was added (to the final mixture). The autoclave was opened, the content was transferred to a 200 ml flask and the solvent was distilled off under reduced pressure, thereby obtaining 4.167 g of a semi-solid oligomer. The catalytic efficiency was 4167 kg Olig/Fe mol. Further, the obtained oligomer had the GPC curve with a single peak, and an Mn of 1300 and an Mw/Mn of 1.2.

Example 2

2.764 g of an oligomer was obtained by the same method as in Example 1 except that the amounts of the diimine compound (1-1) and nickel 2-ethylhexanoate were changed to 5 μmol, respectively. The catalytic efficiency was 2764 kg Olig/Fe mol. Further, the obtained oligomer had the GPC curve with a single peak, an Mn of 940 and an Mw/Mn of 1.3.

Example 3

3.636 g of an oligomer was obtained by the same method as in Example 1 except that nickel acetylacetonate was used in place of nickel 2-ethylhexanoate and the amounts of the diimine compound (1-1) and nickel acetylacetonate were changed to 5 μmol, respectively. The catalytic efficiency was 3636 kg Olig/Fe mol. Further, the obtained oligomer had the GPC curve with a single peak, an Mn of 1300 and an Mw/Mn of 2.7.

Comparative Example 1

4.800 g of a polymer was obtained by the same method as in Example 1 except that the diimine compound (1-1) was not used. The catalytic efficiency was 4800 kg Olig/Fe mol. Further, the obtained polymer had the GPC curve with bi-modal peaks, 30% of which had an Mn of 980 and 70% had 14000.

Comparative Example 2

1.531 g of a polymer was obtained by the same method as in Comparative Example 1 except that nickel acetylacetone was used in place of nickel 2-ethylhexanoate. The catalytic efficiency was 1531 kg Olig/Fe mol. Further, the obtained polymer had the GPC curve with bi-modal peaks, 38% of which had an Mn of 800 and 62% had 130000.

The invention claimed is:

1. A method for preparing an oligomer, comprising:
   a step of oligomerizing a polymerizable monomer comprising an olefin in the presence of a catalyst comprising
   (A) a complex of a diimine compound represented by the following formula (1) and at least one metal selected from the group consisting of Group 8 elements, Group 9 elements and Group 10 elements,
   (B) a mixture of a pyridine diimine compound represented by the following formula (3) and an iron salt and/or an iron complex represented by the following formula (5),
   (C) methylaluminoxane and/or a boron compound, and
   (D) an organoaluminum compound other than methylaluminoxane and/or an organozinc compound:

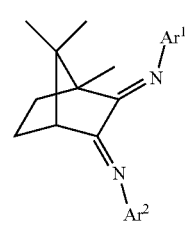

(1)

wherein $Ar^1$ and $Ar^2$ are the same or different and are respectively a group represented by the following formula (2):

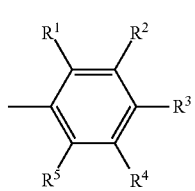

(2)

wherein $R^1$ and $R^5$ are the same or different and are respectively a hydrogen atom or a hydrocarbyl group having 1 to 5 carbon atoms, the total number of carbon atoms of $R^1$ and $R^5$ is 1 or more and 5 or less, and $R^2$, $R^3$ and $R^4$ are the same or different and are respectively a hydrogen atom or an electron-donating group:

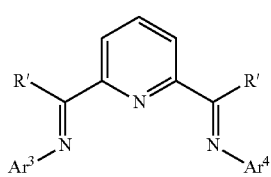

(3)

wherein R' is a hydrocarbyl group having 1 to 6 carbon atoms or an aromatic group having 6 to 12 carbon atoms, a plurality of R' in the same molecule are the same or different, $Ar^3$ and $Ar^4$ are the same or different and are respectively a group represented by the following formula (4):

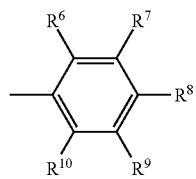
(4)

wherein $R^6$ and $R^{10}$ are the same or different and are respectively a hydrocarbyl group having 3 to 12 carbon atoms or an aromatic group having 6 to 12 carbon atoms, the total number of carbon atoms of $R^6$ and $R^{10}$ is 6 or more, and $R^7$, $R^8$ and $R^9$ are the same or different and are respectively a hydrogen atom or an electron-donating group:

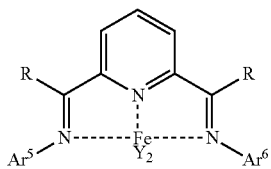
(5)

wherein R is a hydrocarbyl group having 1 to 6 carbon atoms or an aromatic group having 6 to 12 carbon atoms, a plurality of R in the same molecule are the same or different, $Ar^5$ and $Ar^6$ are the same or different and are respectively a group represented by the following formula (6), and Y is a chlorine atom or a bromine atom:

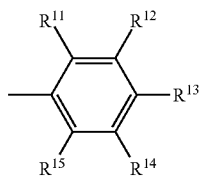
(6)

wherein $R^{11}$ and $R^{15}$ are the same or different and are respectively a hydrocarbyl group having 3 to 12 carbon atoms or an aromatic group having 6 to 12 carbon atoms, the total number of carbon atoms of $R^{11}$ and $R^{15}$ is 6 or more, and $R^{12}$, $R^{13}$ and $R^{14}$ are the same or different and are respectively a hydrogen atom or an electron-donating group.

2. The method according to claim 1, wherein a number average molecular weight (Mn) of the oligomer is 200 to 5000.

3. The method according to claim 1, wherein the organoaluminum compound is at least one selected from the group consisting of trimethylaluminum, triethylaluminum, triisopropylaluminum, tripropylaluminum, tributylaluminum, triisobutylaluminum, trihexylaluminum, triphenylaluminum, diethylaluminum chloride, ethylaluminum dichloride and ethylaluminum sesquichloride.

4. The method according to claim 1, wherein the organozinc compound is at least one selected from the group consisting of dimethylzinc, diethylzinc and diphenylzinc.

\* \* \* \* \*